United States Patent
Viebach et al.

(10) Patent No.: US 10,080,483 B2
(45) Date of Patent: Sep. 25, 2018

(54) SECONDARY ENDOSCOPE MOUNTABLE TO A MOTHER ENDOSCOPE AND A COMBINATION OF A MOTHER ENDOSCOPE AND A SECONDARY ENDOSCOPE

(71) Applicant: Digital Endoscopy GmbH, Friedberg (DE)

(72) Inventors: Thomas Viebach, Waidhofen (DE); Friedrich Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 146 days.

(21) Appl. No.: 15/033,082

(22) PCT Filed: Oct. 28, 2014

(86) PCT No.: PCT/EP2014/073064
§ 371 (c)(1),
(2) Date: Apr. 28, 2016

(87) PCT Pub. No.: WO2015/063051
PCT Pub. Date: May 7, 2015

(65) Prior Publication Data
US 2016/0262601 A1     Sep. 15, 2016

(30) Foreign Application Priority Data
Oct. 30, 2013    (DE) .................. 10 2013 222 039

(51) Int. Cl.
*A61B 1/012* (2006.01)
*A61B 1/00* (2006.01)
(Continued)

(52) U.S. Cl.
CPC .......... *A61B 1/0125* (2013.01); *A61B 1/0057* (2013.01); *A61B 1/00066* (2013.01);
(Continued)

(58) Field of Classification Search
CPC . A61B 1/0052; A61B 1/0057; A61B 1/00066; A61B 1/00039; A61B 1/0051;
(Continued)

(56) References Cited

U.S. PATENT DOCUMENTS

| 3,549,806 A | 12/1970 | Wood |
| 3,605,725 A | 9/1971 | Bentov |

(Continued)

FOREIGN PATENT DOCUMENTS

| CN | 1286664 A | 3/2001 |
| CN | 2762381 Y | 3/2006 |

(Continued)

OTHER PUBLICATIONS

International Search Report dated Mar. 24, 2015 for International Application No. PCT/EP2014/075902.

(Continued)

*Primary Examiner* — Timothy J Neal
(74) *Attorney, Agent, or Firm* — Knobbe, Martens, Olson & Bear LLP

(57) ABSTRACT

The invention refers to a secondary endoscope mountable onto a mother endoscope. The secondary endoscope comprises a grip body (4; 400) having an outer body including an inner channel and an inner body (3; 300) arranged in the inner channel of the outer body, said inner body (3; 300) being movable relatively to the outer body; a catheter (5; 500) mounted on the grip body (4; 400); a control element (1; 100) at the proximal side of the grip body (4; 400) for controlling a bending portion (6; 600) arranged on the distal end of the catheter (5; 500), said control element (1; 100) being arranged on the proximal side of the inner body (3; 300); and a mounting connection on the distal end of the grip body (4; 400) for fixing the secondary endoscope to a mother (Continued)

endoscope (200), said mounting connection being attached to the outer body of the grip body (4; 400).

13 Claims, 12 Drawing Sheets

(51) Int. Cl.
*A61B 1/005* (2006.01)
*A61B 1/05* (2006.01)

(52) U.S. Cl.
CPC ...... *A61B 1/00137* (2013.01); *A61B 1/00163* (2013.01); *A61B 1/05* (2013.01)

(58) Field of Classification Search
CPC ... A61B 1/0053; A61B 1/0055; A61B 1/0056; A61B 1/0125; A61B 2034/742; G02B 23/24; F16C 1/18; G05B 2219/35417; G05B 2219/35438
See application file for complete search history.

(56) References Cited

U.S. PATENT DOCUMENTS

| | | | |
|---|---|---|---|
| 4,241,729 A | 12/1980 | Aoshiro | |
| 4,404,963 A | 9/1983 | Kohri | |
| 4,415,767 A | 11/1983 | Gill et al. | |
| 4,670,009 A | 6/1987 | Bullock | |
| 5,245,133 A | 9/1993 | DeCarlo et al. | |
| 5,569,157 A | 10/1996 | Nakazawa et al. | |
| 5,588,950 A | 12/1996 | Sano | |
| 5,630,419 A | 5/1997 | Ranalletta | |
| 6,383,132 B1 | 5/2002 | Wimmer | |
| 6,547,722 B1 | 4/2003 | Higuma et al. | |
| 6,582,361 B2 | 6/2003 | Hirano | |
| 6,716,160 B2 | 4/2004 | Mitsumori | |
| 7,179,223 B2 | 2/2007 | Motoki et al. | |
| 7,198,599 B2 | 4/2007 | Goto et al. | |
| 7,841,880 B2 | 11/2010 | Ikeda | |
| 2001/0025135 A1 | 9/2001 | Naito et al. | |
| 2002/0040180 A1 | 4/2002 | Hirano | |
| 2002/0115907 A1 | 8/2002 | Mitsumori | |
| 2003/0092965 A1 | 5/2003 | Konomura | |
| 2004/0015050 A1 | 1/2004 | Goto et al. | |
| 2005/0004434 A1 | 1/2005 | Bob et al. | |
| 2006/0116550 A1 | 6/2006 | Noguchi | |
| 2006/0135851 A1 | 6/2006 | Yamazaki | |
| 2006/0199999 A1 | 9/2006 | Ikeda | |
| 2006/0252993 A1 | 11/2006 | Freed | |
| 2007/0156018 A1 | 7/2007 | Krauter et al. | |
| 2007/0221701 A1 | 9/2007 | Ortiz | |
| 2007/0282371 A1 | 12/2007 | Lee | |
| 2009/0209820 A1 | 8/2009 | Tanaka | |
| 2009/0286412 A1 | 11/2009 | Ikeda | |
| 2010/0168560 A1* | 7/2010 | Hauck | A61B 5/06 600/424 |
| 2011/0288372 A1 | 11/2011 | Petersen | |
| 2011/0313252 A1 | 12/2011 | Lin | |
| 2012/0170767 A1 | 7/2012 | Astrom et al. | |
| 2012/0209068 A1 | 8/2012 | Hosaka | |
| 2014/0148646 A1 | 5/2014 | Inada | |
| 2015/0057537 A1* | 2/2015 | Dillon | A61B 1/0014 600/431 |
| 2015/0173711 A1 | 6/2015 | Hiraoka | |

FOREIGN PATENT DOCUMENTS

| | | |
|---|---|---|
| CN | 102307510 A | 1/2012 |
| CN | 102401995 A | 4/2012 |
| CN | 102697445 A | 10/2012 |
| CN | 202748535 U | 2/2013 |
| CN | 103153152 A | 6/2013 |
| CN | 103211566 A | 6/2013 |
| DE | 69 05 185 U | 4/1972 |
| DE | 34 46 698 A1 | 7/1985 |
| DE | 196 27 016 C1 | 2/1998 |
| DE | 697 25 670 T2 | 7/2004 |
| DE | 101 48 099 B4 | 6/2006 |
| DE | 10 2009 060 500 | 7/2011 |
| DE | 102010034623 | 2/2012 |
| DE | 10 2012 009332 | 11/2013 |
| EP | 0 028 396 B1 | 4/1981 |
| EP | 0055394 | 7/1982 |
| EP | 1475031 | 11/2004 |
| EP | 1 759 626 A2 | 3/2007 |
| ES | 2 356 497 | 4/2011 |
| JP | S 48 27116 | 8/1973 |
| JP | S 61 118713 | 6/1986 |
| JP | S 62 227312 | 10/1987 |
| JP | H 06254049 | 9/1994 |
| JP | 10-225439 | 8/1998 |
| JP | H11 244225 | 9/1999 |
| JP | A-2001-061772 | 3/2001 |
| JP | 2001510696 | 8/2001 |
| JP | 2002-160691 | 6/2002 |
| JP | 2002 291699 | 10/2002 |
| JP | 2003 190085 A | 7/2003 |
| JP | 2005 304 586 A | 11/2005 |
| JP | 2007 111541 A | 5/2007 |
| JP | 2007 252921 | 10/2007 |
| JP | 2007313047 | 12/2007 |
| JP | 2009 505688 A | 2/2009 |
| JP | 2009 101134 | 5/2009 |
| JP | 2009 530051 A | 8/2009 |
| JP | 2009 201762 | 9/2009 |
| JP | 2012 245058 A | 12/2012 |
| WO | WO 00/13569 A1 | 3/2000 |
| WO | WO 00/33727 | 6/2000 |
| WO | WO 2005/094665 A2 | 10/2005 |
| WO | WO2008056642 A1 | 5/2008 |
| WO | WO 2009/008596 | 1/2009 |
| WO | WO 2011/108157 A1 | 9/2011 |
| WO | WO 2011/114772 A1 | 9/2011 |
| WO | WO 2013/129204 | 9/2013 |

OTHER PUBLICATIONS

Mar. 2, 2015 Int'l Search Report from related PCT App. No. PCT/EP2014/077938 (3 pgs).
Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Anonymous: "Products | BMP-TAPPI", , Jun. 30, 2013 (Jun. 30, 2013), XP055394249, Gefunden im Internet: URL:https://web.archive.org/web/20130630082009/http :/// www.bmp-tappi.com:80/products [gefunden am Jul. 27, 2017].
Anonymous: "10. Tappo per innesti rapidi femmina", , Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n nesti- rapidifemmina [gefunden am Jul. 27, 2017].
Search Report for Application CN 2015800056419 in 2 pages (English Translation).
Search Report for Application CN 2014800410593 in 2 pages (English Translation).
Search Report for Application CN 201480076051 in 2 pages (English Translation).
Office Action dated Sep. 4, 2017 in 7 pages for Chinese Application No. 201580005641.9.
International Search Report dated Oct. 8, 2014 for International Application No. PCT/EP2014/065587.
International Search Report dated Jan. 13, 2015 for International Application No. PCT/EP2014/073064.
International Search Report dated Jan. 13, 2015 for International Application No. PCT/EP2014/073066.

(56) References Cited

OTHER PUBLICATIONS

International Search Report dated Jan. 19, 2015 for International Application No. PCT/EP2014/073065.

* cited by examiner

SECONDARY ENDOSCOPE MOUNTABLE TO A MOTHER ENDOSCOPE AND A COMBINATION OF A MOTHER ENDOSCOPE AND A SECONDARY ENDOSCOPE

CROSS REFERENCE TO RELATED APPLICATIONS

This application is a U.S. National Phase of PCT International Application No. PCT/EP2014/073064, filed Oct. 28, 2014 and which claims priority benefit of German Patent Application No. 102013222039.1 filed on Oct. 30, 2013. The entirety of each of the above-identified applications is hereby incorporated by reference.

BACKGROUND

Field of the Invention

The present invention relates to a secondary endoscope which is mountable to a mother endoscope. The present invention further relates to a combination of a mother endoscope and a secondary endoscope.

Description of Related Art

In an endoscope, a bendable end of a catheter, i.e. a so-called deflecting portion, is moved by pivoting a control element, wherein the movement of the deflecting portion precisely follows the movement of the control element.

When carrying out a medical examination by means of an endoscope, the transmission of a pivoting movement of a control element to a bending movement of the deflecting portion should be as precise as possible. On the other hand, the transmission of a pivoting movement of a control element to a bending movement of the deflecting portion should be easily and straightforwardly executable for the user.

SUMMARY

It is the object of the present invention to provide an improved secondary endoscope mountable onto a mother endoscope.

In particular, it is the object of the present invention to provide a secondary endoscope which is particularly favorable in functionality and easy to use and the handling of which during the pivoting movement of the control element is improved. Besides, an improved combination of a mother endoscope and a secondary endoscope is to be provided.

According to the invention, this problem is solved by a secondary endoscope comprising the features of claim 1.

A combination of a mother endoscope and a secondary endoscope is indicated in claim 11. An alternative combination of a mother endoscope and a secondary endoscope is indicated in claim 12.

The dependent claims deal with advantageous further developments.

Thus, the invention relates to a secondary endoscope mountable onto a mother endoscope and comprising a grip body; a catheter mounted on the grip body; a control element on the proximal side of the grip body for controlling a deflecting portion arranged on the distal end of the catheter (bending portion); and a mounting connecting piece on the distal side of the grip body for fixing the secondary endoscope to a mother endoscope.

The grip body as base element of the secondary endoscope has the control element on its proximal side, and the mounting connecting piece to the mother endoscope on its distal side. The control element is easily operable by the user as it stretches out towards him/her.

The grip body can comprise a catheter channel for guiding the catheter. The catheter channel can be an inner channel inside the grip body. In this secondary endoscope, the catheter including the deflecting portion can be passed through the control element controlling the deflection movement of the deflecting portion. Thus, a secondary endoscope is provided for enabling a safe and clear handling of a pivoting movement of a deflecting portion, even in the narrowest of spaces. The inner channel can be arranged concentrically in the grip body. The stability of the entire device is not adversely affected thereby.

The proximal end of the control element can have a proximal inlet opening of the catheter channel. Moreover, the proximal inlet opening of the catheter channel in the grip body can comprise a funnel-shaped inlet opening as insertion aid. This enables a safe guidance of the catheter to be passed therethrough.

The proximal end of the catheter can be mounted on the distal end of the grip body.

The proximal end of the catheter can be mounted on the outer side of the grip body. Thus, the distance from the attachment point of the catheter on the grip body to the proximal inlet opening of the catheter channel can be made short, wherein the grip body construction as such can be short, even if a catheter connecting portion on the grip body extends in the distal direction.

The distal end of the grip body can comprise a mounting body for being assembled with the mother endoscope, said mounting body comprising a portion of the catheter channel for guiding the catheter.

The mounting body can be provided with a marking providing information about the mounted or demounted state.

The mounting body can be a Luer lock connecting element, a screw top element, a bayonet locking element, or a snap connection element.

The control element can be pivotable for pivoting the deflecting portion and can be provided, on its proximal side, with markings providing information about the pivoting direction of the deflecting portion. Thus, the control element is a pivoting portion which is supported on a head portion of the base body and is pivotable relative to the head portion of the base body for achieving a deflecting movement. Thus, the control element is pivotable and the deflecting portion is controlled by its pivoting movement. The control element can be lockable so as to lock a deflected position of the control element. The control element can be a joystick.

An inventive combination of a mother endoscope and a secondary endoscope is provided with a mother endoscope having an access connecting piece for a secondary endoscope on the distal side of a mother endoscope grip, and a secondary endoscope which is detachably mounted on the access connecting piece and comprises a secondary endoscope grip and a catheter, wherein the catheter of the secondary endoscope is guided through a catheter channel of the secondary endoscope grip, wherein the distal end of the secondary endoscope grip is detachably mounted on the access connecting piece of the mother endoscope, wherein, in its mounted position, the secondary endoscope on the mother endoscope grip is detachably mounted on the proximal side of the access connecting piece of the mother endoscope, wherein a catheter inlet opening is positioned on the secondary endoscope proximally from the mounting place of the secondary endoscope.

The secondary endoscope grip can further comprise an additional channel inlet opening on its proximal side and a fluid inlet opening on its distal side.

The features of the invention can be suitably combined.

In the following, the invention will be explained in detail by means of examples.

DETAILED DESCRIPTION OF THE DRAWINGS

Figure 1:
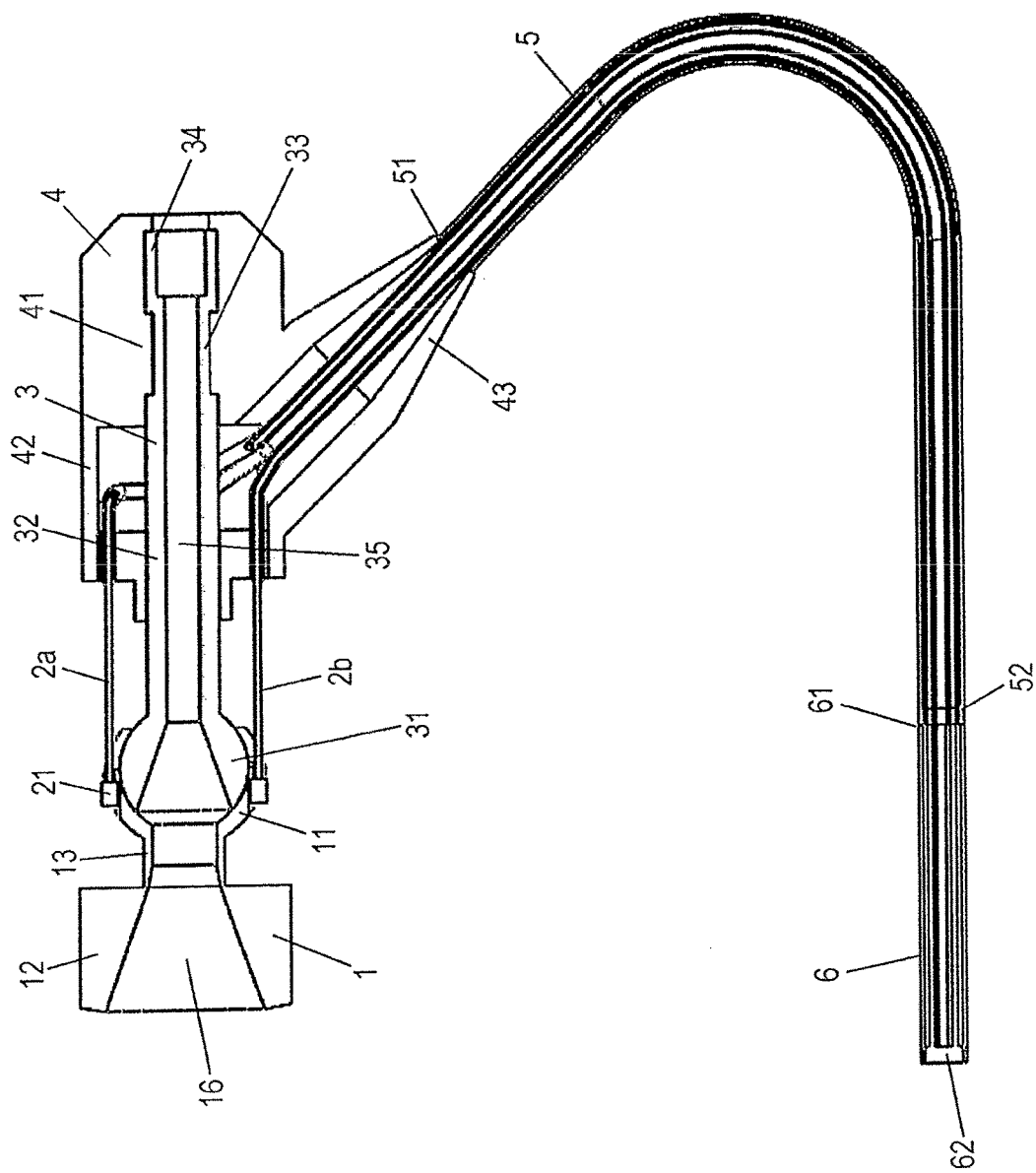
FIG. 1 shows a schematic sectional view of a secondary endoscope of a first embodiment in a non-deflected state.

In the following, embodiments of the present invention will be described in detail by means of the drawings.

First Embodiment

First of all, a first embodiment of the present invention will be described in detail by means of FIGS. 1-7.

The first embodiment shows an inventive secondary endoscope in which an endoscope deflecting control is carried out by a control element.

In the present embodiment, this secondary endoscope consists of a control element 1, several wire bodies 2, a rod element 3 as base element, a rod element holder 4, a catheter tube 5 and a deflecting portion 6.

The control element 1 consists of a hollow cylindrical element having a control head 12, on the lower side of which a hollow shaft 13 is centrically arranged and turns into a hollow ball portion 11, on the outer surface of which the wire bodies 2 are anchored. The hollow ball portion 11 is open on its side facing away from the head 12. In particular, the opening on the hollow ball portion 11 is such that the hollow ball portion 11 makes up approximately 9/10 of a ball, approximately 1/10 of which has been cut off.

The control element 1 is configured in a rotationally symmetrical configuration and comprises an inner channel 16 concentrically extending through the head 12, the hollow shaft 13 and the hollow ball portion 11. The inner channel 16 is expanded in the head 12 such that its inner diameter increases towards the side of the head 12 facing away from the hollow ball portion 11, as is shown in FIG. 1. Thus, the inner channel 16 of the head 12 has a funnel-shaped inlet opening, which is shown in FIG. 1 on the left side of the inner channel 16. The funnel-shaped inlet opening of the inner channel 16 makes it easier to insert the deflecting portion 6 into the inner channel 16.

The control element 1 is made of a plastic material.

The control element 1 is seated as a joystick on a head 31 of the rod element 3. In particular, the hollow ball portion 11 of the control element 1 is seated on a counter-ball portion 31, which forms the head of the rod element 3. The counter-ball portion 31 is configured such that it has a ball shape of such a size that the hollow ball portion 11 seated thereon is smoothly movable. The dimensional relations between the counter-ball portion 31 and the hollow ball portion 11 are such that a relative movement of the control element 1 to the rod element 3 is possible without the user having to exert much force but that, on the other hand, the hollow ball portion 11 is not seated loosely on the counter-ball portion 31.

The rod element 3 has a longitudinal cylinder 32 which, on its distal side, turns into the counter-ball portion 31 and, on its distal end portion, has a screw end 34 which, in the present embodiment, is formed as an inner square. Proximally from the square end 34, the rod element 3 has an outer threaded portion 33 on its outer cylindrical surface. The rod element 3 is configured to be rotationally symmetrical and has, in its interior, an inner channel 35, which extends concentrically through the counter-ball portion 31, the longitudinal cylinder 32 and the square end 34. Besides, the counter-ball portion 31, the longitudinal cylinder 32 and the square end 34 are designed as an integral rod element. The longitudinal cylinder 32 of the rod element 3 is formed as a cylinder having a smooth outer surface, except for the threaded portion 33 provided thereon.

On the counter-ball portion 31, the inner channel 35 has a funnel-shaped inlet opening, which FIG. 1 shows on the left side of the inner channel 35. The funnel-shaped inlet opening of the inner channel 35 is opposite to the outlet opening of the inner channel 16 on the hollow ball portion 11 and makes it easier to insert the deflecting portion 6 into the inner channel 35.

As is shown in the Figures, the rod element 3 is seated in a rod element holder 4. The rod element holder 4 forms the grip body of the secondary endoscope and consists of a cylinder element 42, which is of a rotationally symmetrical construction and has a central inner channel. The cylinder element 42 particularly comprises a cavity facing the control element 1 and a bottom on the side of the rod element holder 4 facing away from the control element 1. More precisely, the bottom of the rod element holder 4 comprises the concentric inner channel. An internal thread 41 is formed in the concentric inner channel. As is schematically shown in the Figures, the outer thread 33 of the rod element 3 is seated on the internal thread 41 of the rod element holder 4, wherein, by a screwing movement, the rod element 3 can be concentrically screwed in or out relatively to the rod element holder 4. For the purpose of performing the screwing movement, a suitable tool is inserted into the square end 34 of the rod element 3. Other relative moving techniques are possible, as is shown under "Alternatives" at the end of the description.

The cylinder element 42 of the rod element holder 4 has a catheter connecting element 43 at its outer peripheral side. In the present embodiment, the catheter connecting element 43 extends at an acute angle relatively to the cylinder element 42 of the rod element 4, as is shown by the drawings.

In particular, the catheter connecting element 43 is formed as a round hollow profile, which roughly constitutes a channel branch from the distal cavity of the cylinder element 42. The catheter connecting element 43 is formed as a cylinder, tapering in a direction away from the cylinder element 42. Inside, the catheter connecting element 43 has a concentric channel in which the wire bodies 2 are guided. At its distal end, the catheter connecting element 43 has a circular port.

The catheter tube 5 is fixed to the circular port of the catheter connecting element 43. In particular, the proximal end 51 of the catheter tube 5 is seated on the port of the catheter connecting element 43. At its distal end, the catheter tube has a ring 52 incorporated therein. The ring 52 forms the distal end of the catheter tube and the transition to the deflecting portion 6.

The deflecting portion 6 is a bendable body which is made of an elastic material in a known manner. At its proximal end, the deflecting portion has a deflecting connection 61 at which it is connected to the ring 52 of the catheter tube 5. At its distal end, the deflecting portion has a deflecting cap 62, at which a camera, a laser and/or a camera, etc. are arranged. Further functional units can be integrated at the deflecting cap 62.

Figure 4:
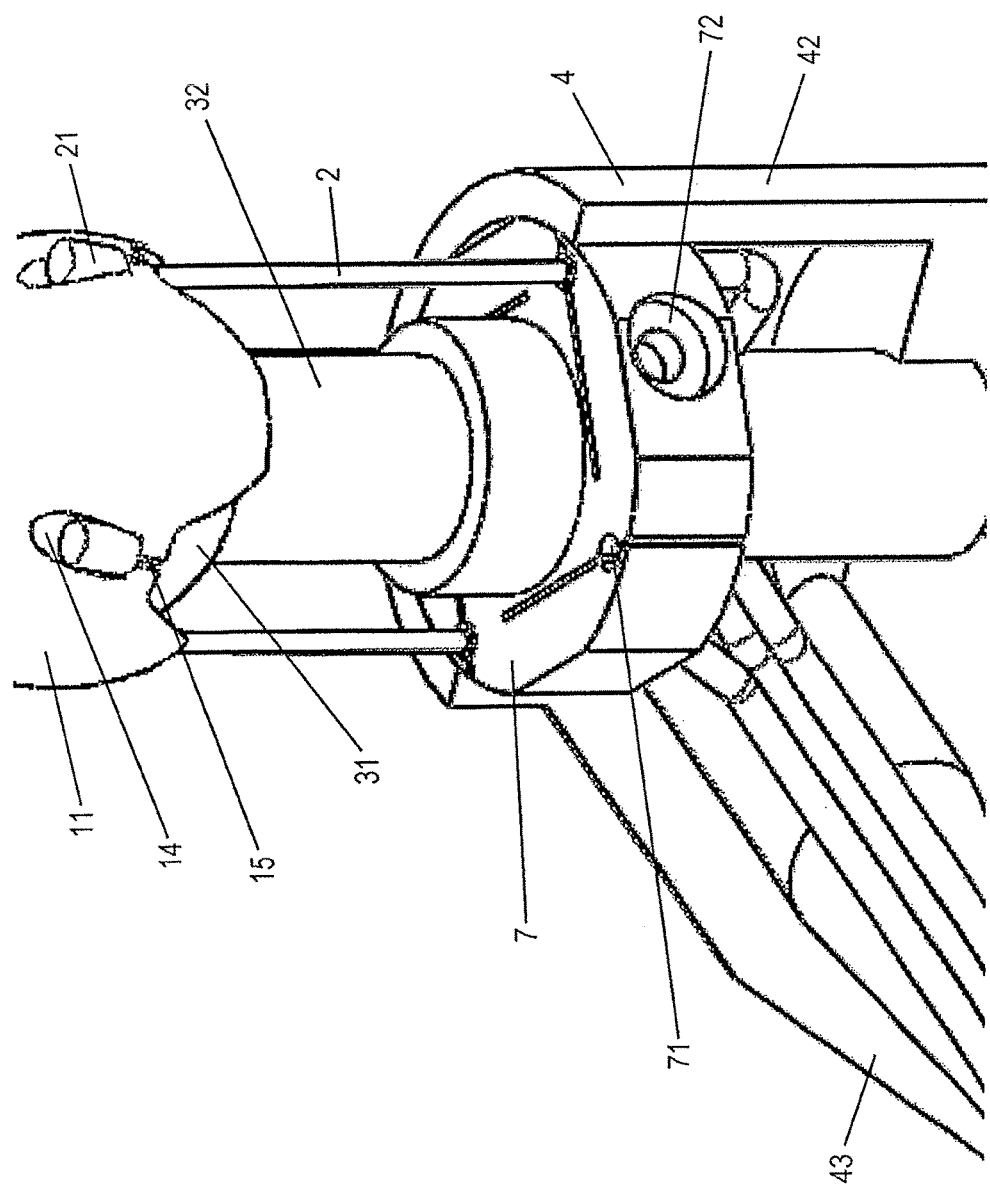
FIG. 4 shows, in a schematic sectional view in perspective, details of the attachment of the wire bodies on the control element and how the wire bodies are guided to the catheter tubes.
Figure 5:
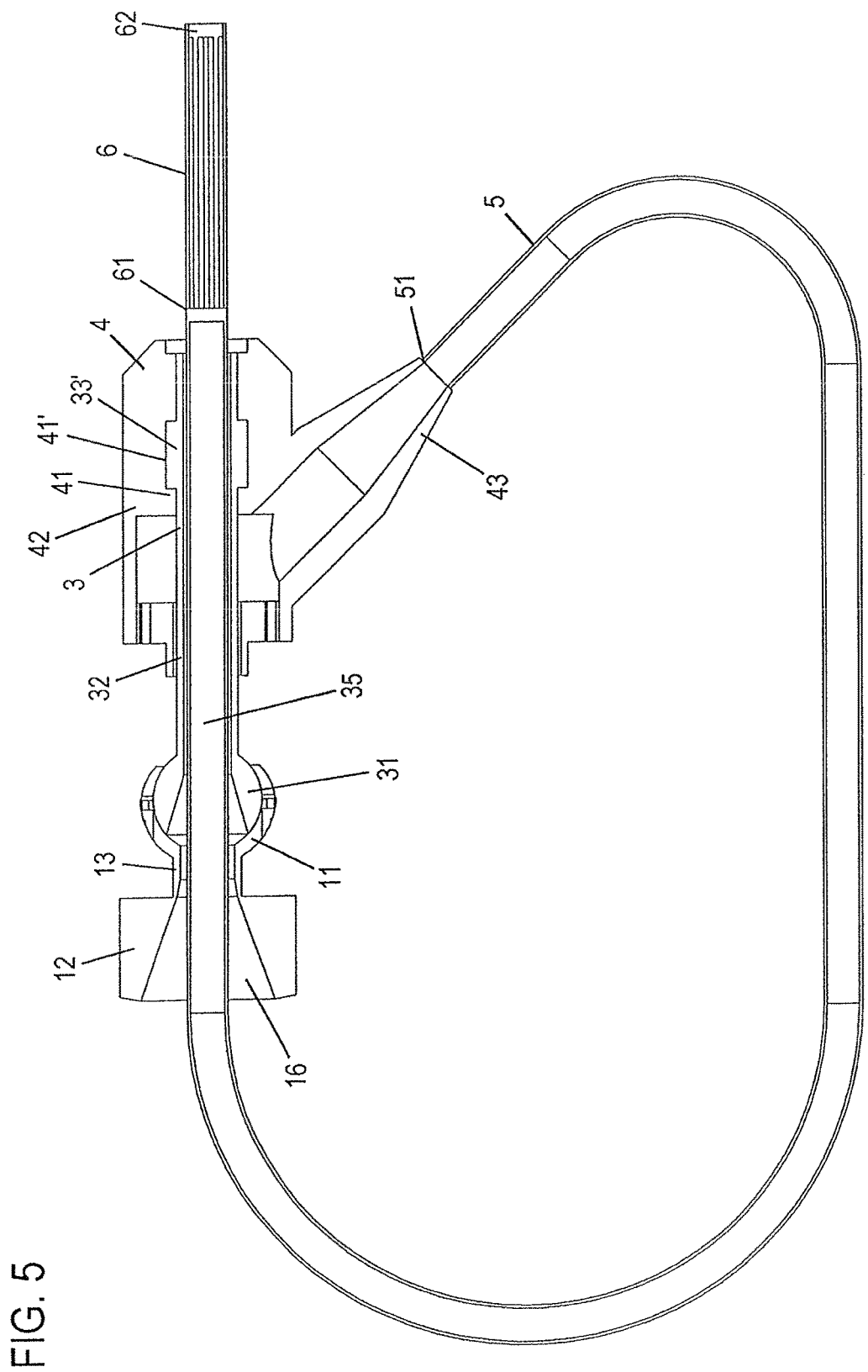
FIG. 5 shows a schematic sectional view of the secondary endoscope of the first embodiment, wherein the catheter tube is guided through the secondary endoscope and is not deflected.
Figure 6:
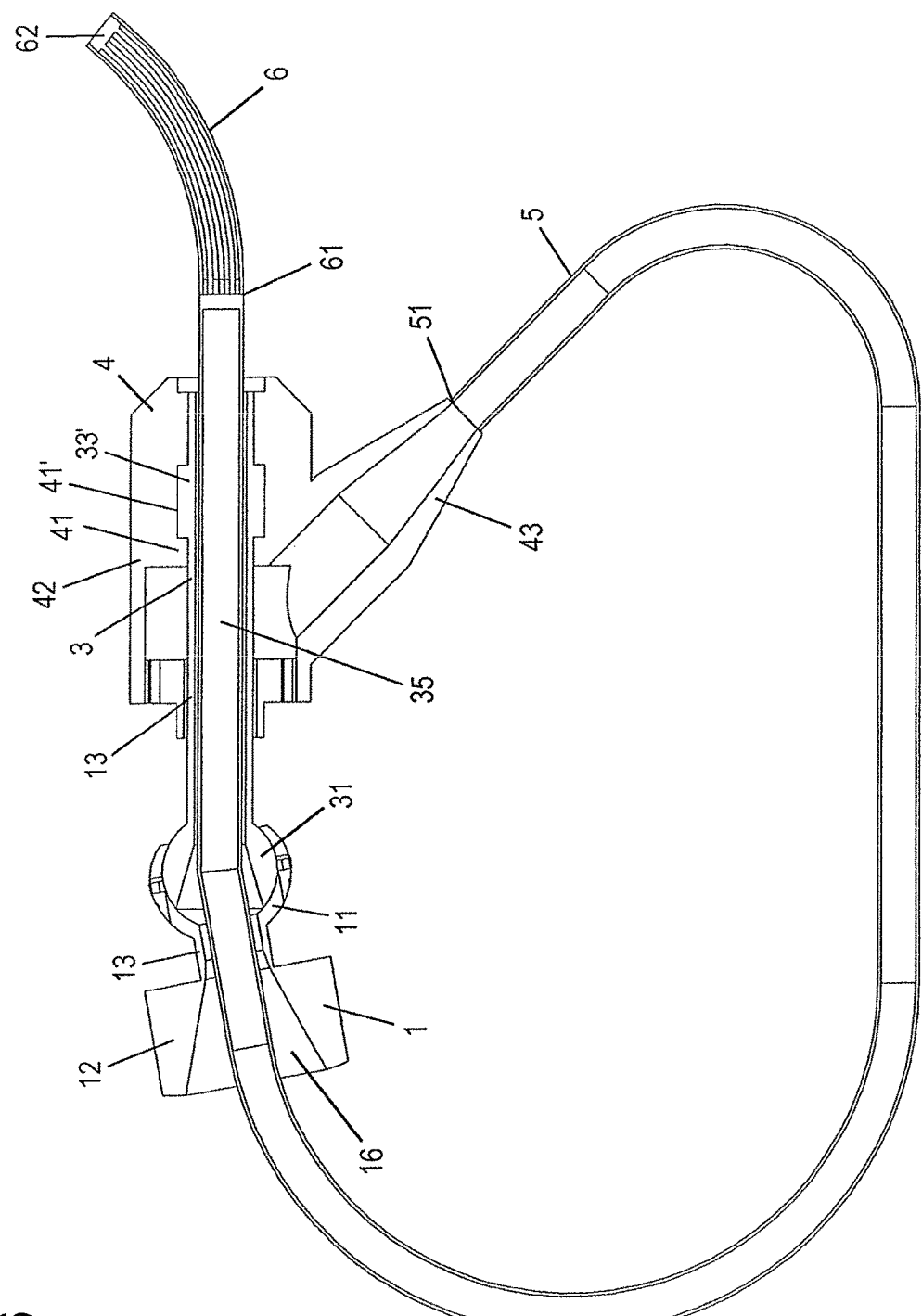
FIG. 6 shows a schematic sectional view of the secondary endoscope, wherein the catheter tube is conducted through the secondary endoscope and a deflection to the left has been made.
Figure 7:
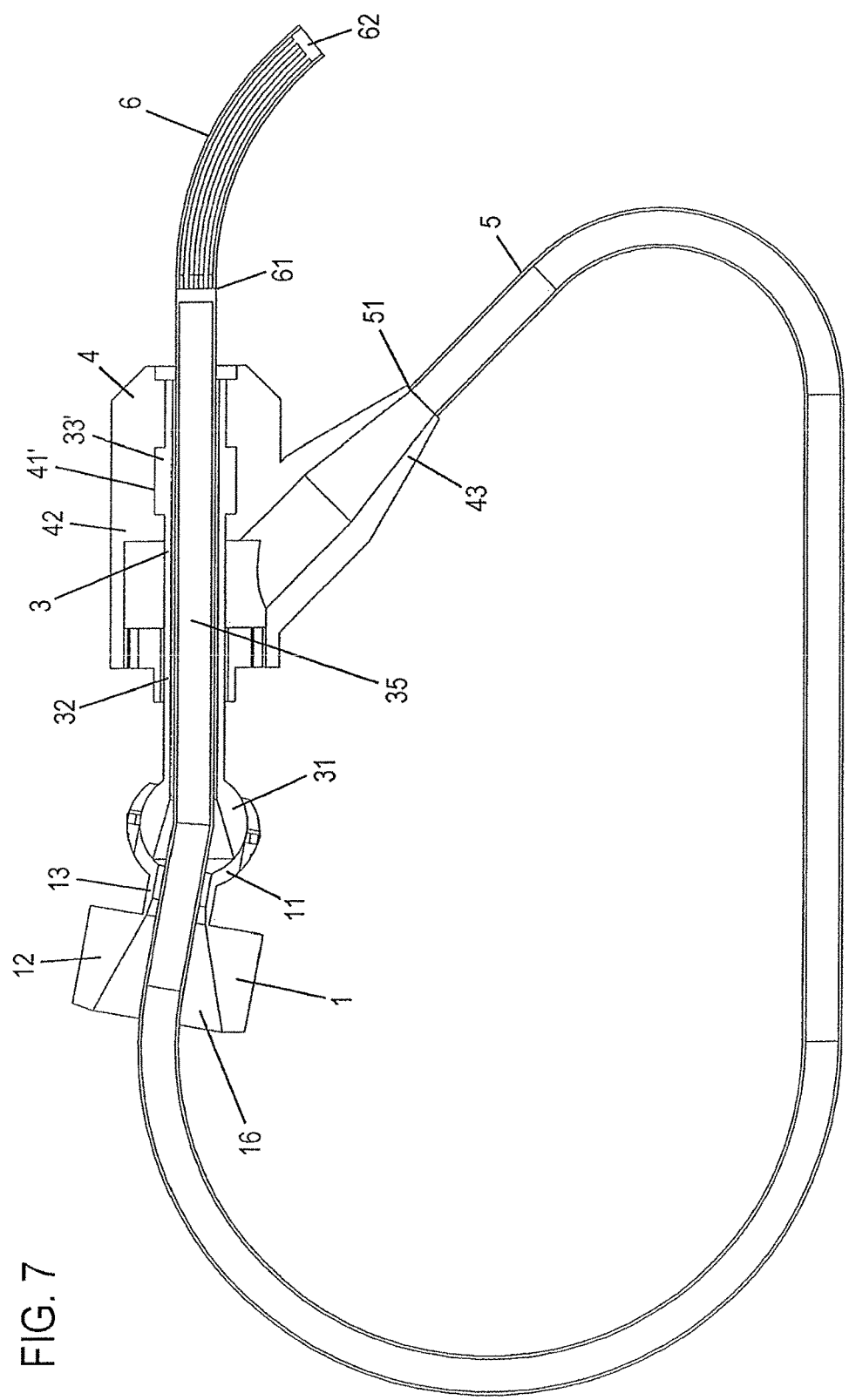
FIG. 7 shows a schematic sectional view of the secondary endoscope, wherein the catheter tube is guided through the secondary endoscope and a deflection to the right has been made.

In a schematic partial perspective view FIG. 4 shows particulars of the connection of the wire bodies to the control element and how the wire bodies are guided to the catheter tube. So as to improve clarity, the front wire body 2 on the left has been omitted in FIG. 4.

As is shown in FIG. 4, several hang-in cavities 14 are provided in the outer circumferential surface of the hollow ball portion 11 at the equatorial line of the hollow ball portion 11. In the present embodiment, four hang-in cavities 14 are provided at the equator of the hollow ball portion 11. In particular, the hang-in cavities 14 are recesses with a bottom, formed in the hollow ball portion 11 and circular in cross-section, wherein the bottom extends approximately perpendicularly to a borehole direction of the hang-in cavity 14 and is located at the equatorial line, more precisely, perpendicularly to the equator of the hollow ball portion 11. When manufacturing the hang-in cavity 14, the hollow ball portion 11 can be drilled from the proximal side, so that the hang-in cavity is produced as a laterally open blind hole in the outer circumferential surface of the hollow ball portion 11. Any other manufacturing methods can be applied. The outer diameter of the hang-in cavity 14 is selected such that a barrel nipple 21 of the wire body 2 fits in the hang-in cavity 14. At the bottom of the hang-in cavity 14, i.e. at the distal end of the hang-in cavity 14, a channel 15 is formed as wire body hang-in; it extends coaxially to the longitudinal extension of the control element 1 and has a diameter which is larger than the outer diameter of the wire body 2, but smaller than the outer diameter of the barrel nipple 21 of the wire 2. In other words, similarly to Bowden cable mountings on the bicycle, the hang-in cavity 14 and the wire body hang-in 15 are provided such that a barrel nipple 21 of a wire body 2 can be hung in. In the hung-in state of the wire body 2, the barrel nipple forms the proximal end of the wire body 2.

Figure 2:
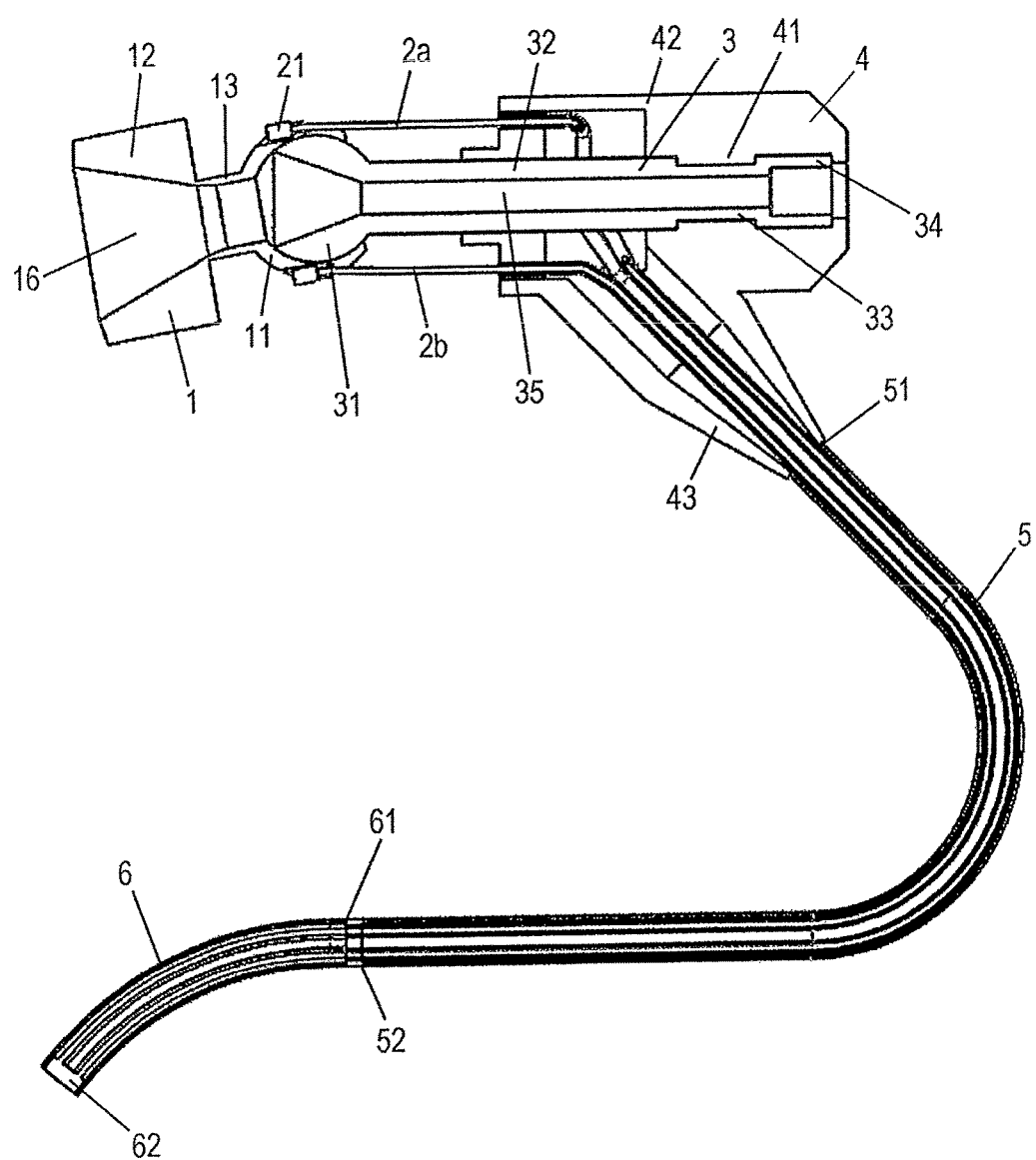
FIG. 2 shows a schematic sectional view of the secondary endoscope during a deflection towards the left.
Figure 3:
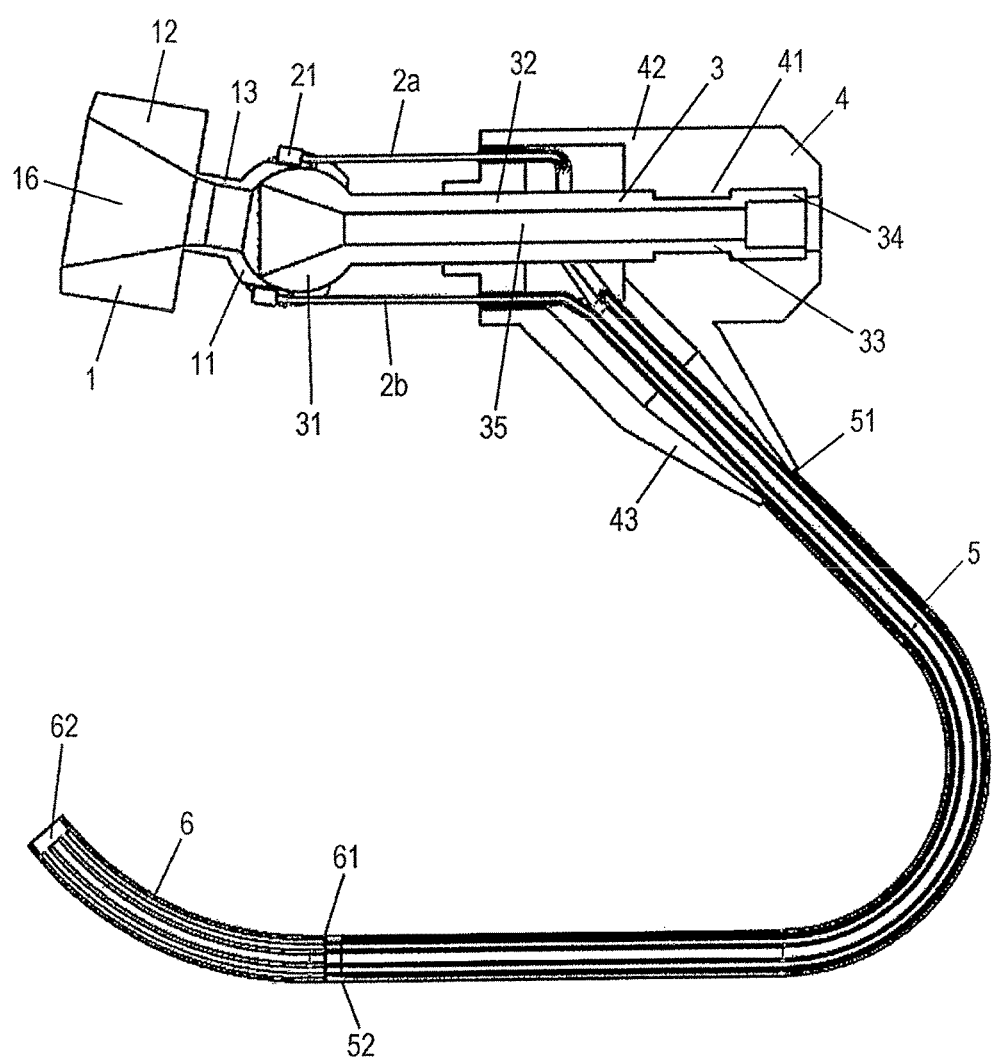
FIG. 3 shows a schematic sectional view of the secondary endoscope during a deflection to the right.

In the present embodiment, four wire bodies 2 are provided; in FIGS. 1 to 3, two wire bodies, i.e. wire body 2a and wire body 2b, are shown, respectively. The number of wire bodies 2 is not limited here. One wire body 2, 2, 3, 4 can be provided, or several ones. Should two or more wire bodies 2 be provided, the corresponding hang-in cavities 14 are equally spaced and arranged on the equator of the hollow ball portion 11.

As is shown in FIG. 4, the cylinder element 42 has the opening to the cylinder element cavity at its proximal end, i.e. at its end facing the control element 1. A wire body guiding ring 7 is inserted into said opening such that the proximal surface, i.e. the surface of the wire guiding ring 7 facing the control element 1 aligns with the proximal front face of the cylinder element 42, i.e. the one facing the control element 1. The wire guiding ring 7 is provided with the same number of tangential slits as there are wire guides 2, as is shown in FIG. 4. Wire guiding bores 71 are drilled in the slits and extend coaxially to the common axis of the control element 1, rod element 4 and the cylinder element 42 of the rod element holder 4. More specifically, the distance of each hang-in cavity 14 to the central axis of the control element 1 is as large as the radial distance between the wire guiding bore 71 and the central axis of the wire guiding ring 7.

The wire bodies 2 are guided through the catheter tube 5 and through the ring 52 of the catheter tube and are anchored to the deflecting cap 62 of the deflecting portion 6. In particular, the wire bodies 2 are anchored to the deflecting cap 62 such that they are spaced equally to each other and are arranged, i.e. fixed, in the same order as on the hollow ball portion 11.

The ring 52 comprises openings for the wire bodies 2 analogously to the design of the wire guiding ring 7.

Functioning/Operation

The control element 1 is configured and can be operated in the same way as a joystick, wherein its hollow ball portion 11 can be moved on the counter-ball portion 31 of the rod element 3. In this way, it is possible to pivot the joystick 1 relatively to the rod element 3 in any direction whatsoever. The direction and the extent of the deflecting movement of the joystick 1 relative to the rod element 3 is then transmitted by the wire bodies 2 arranged on the deflecting cap 62 to the deflecting portion 6 configured as a bendable body. In other words, when the joystick 1 is moved to the left relative to the rod element 3, the deflecting portion 6 executes a movement to the left, as is shown in FIG. 2. When the joystick 1 is moved to the right relative to the rod element 3, the deflecting portion 6 executes a movement to the right, as is the case in FIG. 3.

Prior to the introduction of the deflecting portion 6, the control element 1 is set straight, so that the deflecting portion 6 and the portion of the catheter tube 5 which is adjacent to the deflecting portion 6 are made to be straight. The distal end (on the deflecting cap 62) of the deflecting portion 6 is inserted into the funnel-shaped inlet opening of the inner channel 16 in the control element 1, is slid through the inner channel 16, is inserted into the funnel-shaped inlet opening of the inner channel 35 in the rod element 3, and is slid through the inner channel 35 until the deflecting portion 6 emerges at the outlet opening of the inner channel 35 which is opposite to the inlet opening of the inner channel 35.

When the deflecting portion 6 has reached its intended operational position, i.e. the position in which it is slid through the secondary endoscope, the deflecting portion 6 can be brought into the desired pivot position by turning of the control element 1 in the desired direction and to the desired extent. The control element 1 as joystick can turn in all directions and, thus, the deflecting portion 6 cannot only turn to the right and left, but in all directions.

Second Embodiment

In the following, a second embodiment of the present invention will be described in detail by means of FIGS. 8 to 11.

The second embodiment shows a secondary endoscope, in which an endoscope deflecting control is carried out by a control element.

In the present embodiment, too, said secondary endoscope consists of a control element 100, several wire bodies (not shown in the drawings) in a similar manner as in the first embodiment, a rod element 300 as base element, a rod element holder 400, a catheter tube 500 and a deflecting portion 600.

The control element 100 consists of a cylindrical element having a control head 120 on the lower side of which a shaft portion 130 is centrally arranged. The shaft portion 130 has a foot portion 110 at the end opposite to the control head 120. The shaft portion 130 has a constant outer diameter. The foot portion 110 has an outer diameter increasing in the direction opposite to the control head 120.

Figure 9:
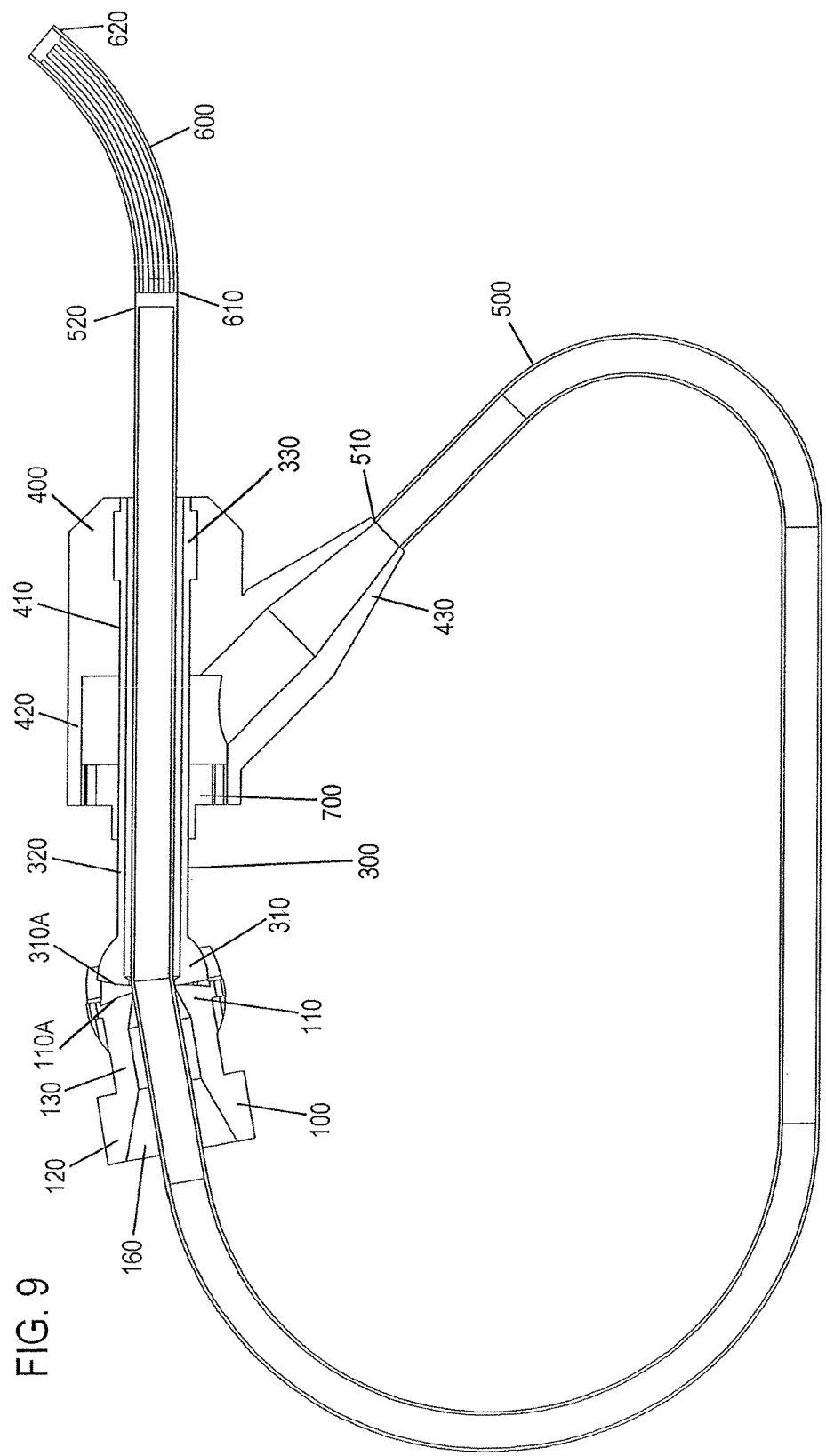
FIG. 9 shows a schematic sectional view of the secondary endoscope of the second embodiment, wherein the catheter tube is guided through the secondary endoscope and a deflection to the left has been made.

The control element 100 is built up in a rotationally symmetrical configuration and comprises an inner channel 160 concentrically extending through the head 120, the shaft portion 130 and the foot portion 110. The inner channel 160 is enlarged in the head 120 such that its inner diameter increases towards the side facing away from the foot portion 110, as is shown in FIG. 9. Thus, the inner channel 160 of the head 120 has a funnel-shaped inlet opening, which is shown in FIG. 9 on the left side of the inner channel 160. The funnel-shaped inlet opening of the inner channel 160 makes it easier to insert the deflecting portion 600 into the inner channel 160. The funnel-shaped inlet opening of the inner channel 160 is rounded, so that it does not have any sharp edges.

The control element 100 pivots on the foot portion 110 relative to the rod element 300; therefore, the foot portion 110 of the control element 100 is designated as pivot portion 110.

The pivot portion 110 has an end face formed as foot surface 110A on the side opposite to the control head 120. In the present embodiment, the foot surface 110A is outwardly bulged, i.e. it is curved outwards opposite to the front surface of the control head 120 which comprises the funnel-shaped inlet opening of the inner channel 160. In other words, the distance measured in the longitudinal direction of the cylindrical control element 100 between the foot surface 110A and the front surface of the control head 120 opposite to the foot increases from the outer circumference to the middle. Therefore, the foot surface 110A forms a portion of a ball surface having a predetermined radius, whose center is located on the assumed prolonged axis of the control element 100.

The inner channel 160 has its outlet opening at the foot surface 110A. The inner channel 160 tapers in the area of the foot portion 110 and reaches its smallest inner diameter at the foot surface 110A. At the outlet opening, the inner channel 160 is rounded, so that it does not have any sharp edges.

At its narrowest point, the inner channel 160 has an inner diameter which, on the one hand, still allows a safe sliding-through of the deflecting portion 600 and the catheter tube 500 and, on the other hand, forms a guide for the deflecting portion 600 and the catheter tube 500 when these are passed through.

Figure 10:
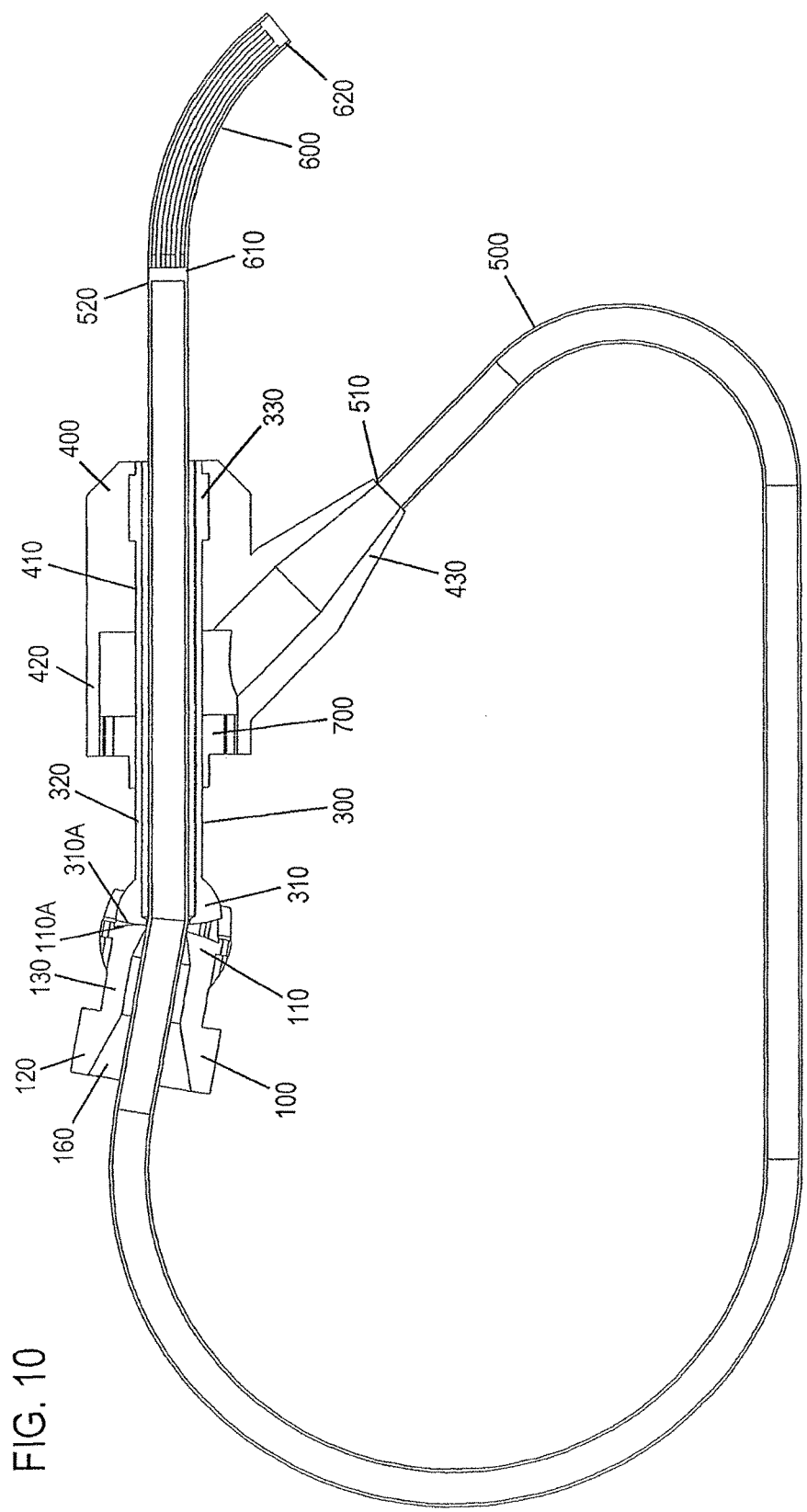
FIG. 10 shows a schematic sectional view of the secondary endoscope of the second embodiment, wherein the catheter tube is guided through the secondary endoscope and a deflection to the right has been made.
Figure 11:
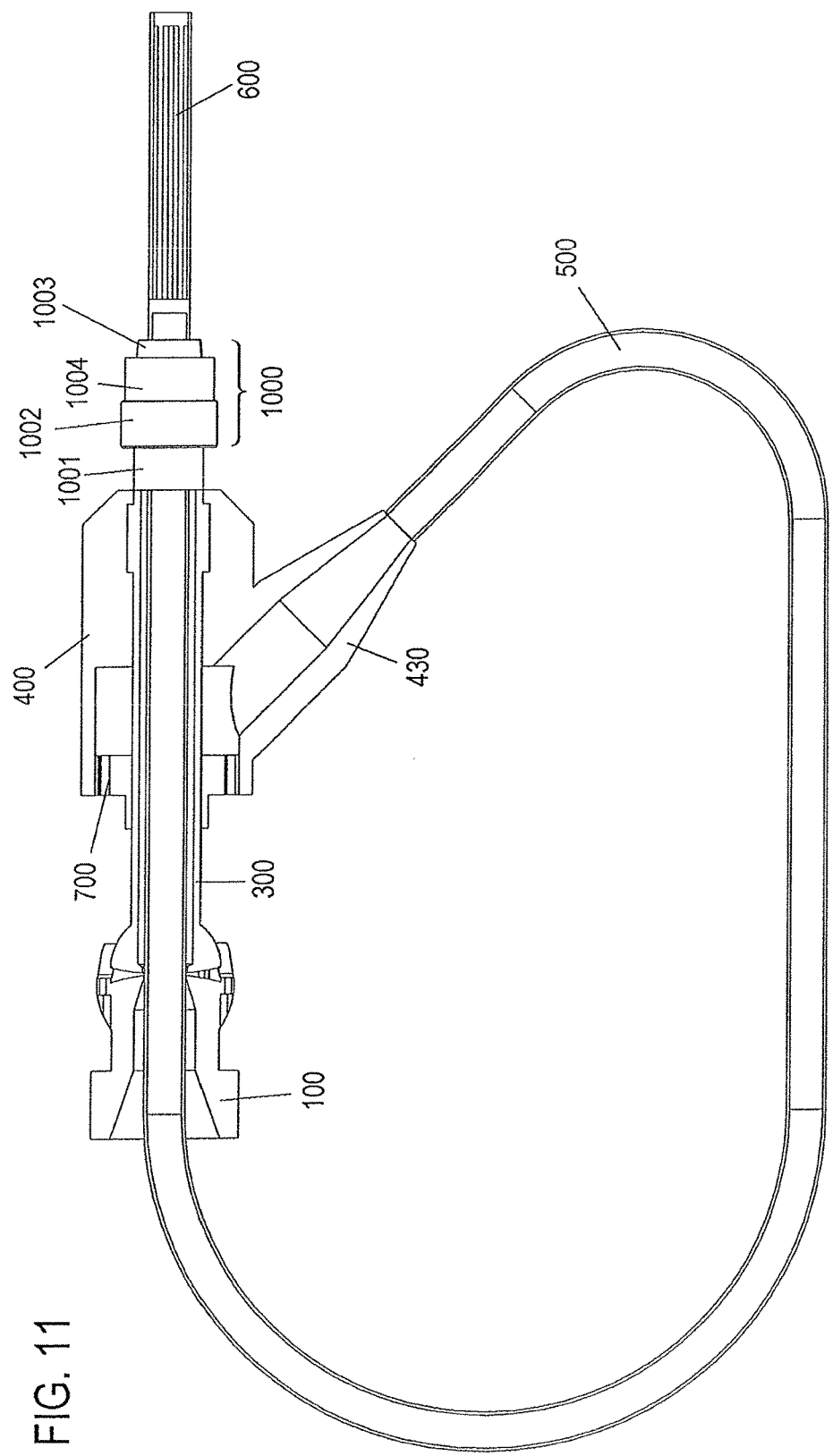
FIG. 11 shows a schematic sectional view of the secondary endoscope of the second embodiment, wherein a mounting body for assembly with the mother endoscope is positioned on the distal side of the grip body.

The control element 100 is rotationally symmetrical, as can be seen in FIGS. 9 to 11. The control element 100 is made of a plastic material, but can also be made of metal.

A front surface 310A of a head portion 310 of the rod element 300 is opposite to the foot surface 110A of the pivot portion 110, as is shown in FIGS. 9 to 11.

The rod element 300 has a longitudinal cylinder 320 which turns into the head portion 310 at its proximal side and has an increased-diameter portion 330 in the vicinity of its distal end portion. The increased-diameter portion 330 is provided as a cylinder portion which has a larger outer diameter than in the portion between the head portion 310 and the increased-diameter portion 330. The rod element 300 has a rotationally symmetrical configuration.

Thus, the rod element 300 is an integral elongated element comprising the head portion 310, the longitudinal cylinder 320 and the increased-diameter portion 330. The longitudinal cylinder 320 of the rod element 300 is formed with a smooth outer surface.

The rod element 300 has a rotationally symmetrical configuration and comprises an inner channel 350 which concentrically extends through the head portion 310, the longitudinal cylinder 320 and the increased-diameter portion 330. The inner channel 350 is narrowed at the head portion 310. At the front surface 310A of the head portion 310, the inner channel 350 has its inlet opening, at which the inner channel 350 has its smallest inner diameter. The inner channel 350 is rounded at the inlet opening so that it does not have any sharp edges. Downstream of the inlet opening, the inner channel 350 has an even inner diameter, which is larger than at the head portion 310. At the outlet opening, too, the inner channel 350 is rounded, so that it does not have any sharp edges. On the one hand, the narrowing of the inner diameter at the head portion 310 still allows a safe sliding-through of the deflecting portion 600 and the catheter tube 500 and, on the other hand, forms a guide for the deflecting portion 600 and the catheter tube 500 when these are inserted.

In the present embodiment, the front surface 310A is also bulged outwardly towards the control element 100. In other words, the foot surface 110A raises from the outer circumference towards the middle in the direction of the control element 100. The front surface 310A forms a portion of a spherical surface having a predetermined radius whose center is positioned on the assumed elongated axis of the rod element 300.

The foot surface 110A and the front surface 310A face each other and are in contact with each other. Thus, the pivot portion 110 of the control element 100 is pivotably seated, with its foot surface 110A, on the front surface 310A of the head portion 310 of the rod element 300. In other words, the foot surface 110A can roll on the front surface 310A.

Figure 8:
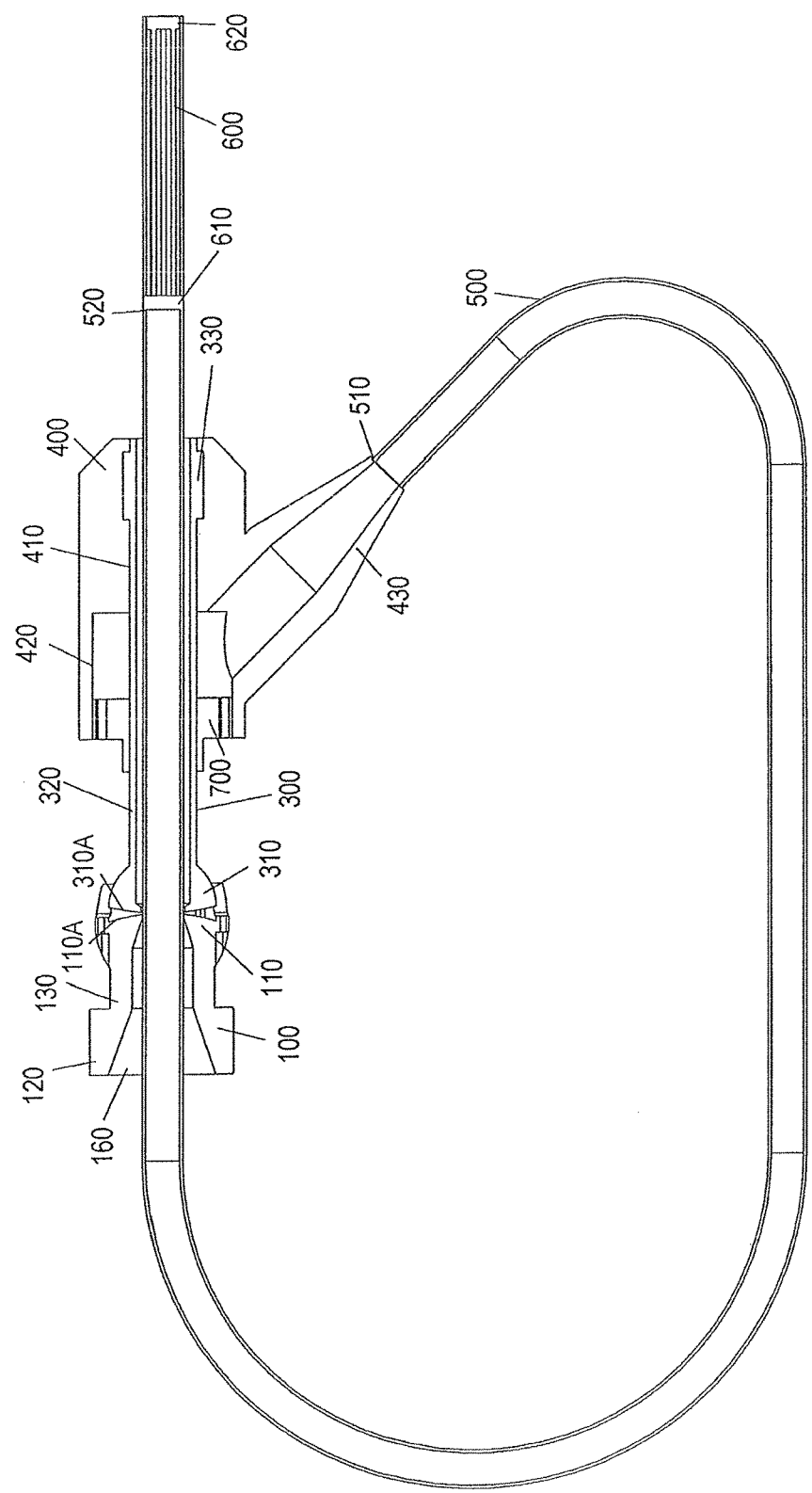
FIG. 8 shows a schematic sectional view of a secondary endoscope of a second embodiment, wherein the catheter tube is guided through the secondary endoscope and is not deflected.

In its non-pivoted state, the pivot portion 110 of the control element 100 and the head portion 310 of the rod element 300 are on the same central axis as, in the non-pivoted state, the control element 100 and the rod element 300 are arranged coaxially to each other. Thus, in the non-pivoted state, the foot surface 110A and the front surface 310A touch each other at a circular line, as is shown in FIG. 8. When the control element 100 is pivoted, as is shown in FIGS. 9 and 10, i.e. the pivot portion 110 is inclined relative to the head portion 310 of the rod element 300, the foot surface 110A rolls on the front surface 310A. It shall be pointed out here that the view in the drawings is a schematic view only.

Thus, the control element 100 is seated as a joystick on the head portion 310 of the rod element 300.

The rod element 300 is arranged in the rod element holder 400. The rod element holder 400 forms the grip body of the secondary endoscope and is formed as cylinder element 420 which has a rotationally symmetrical configuration. On the side facing the control element 100, the cylinder element 420 comprises a cavity, and the cylinder element 420 comprises a bottom on the side of the rod element holder 400 facing away from the control element 100. The bottom of the rod element holder 400 comprises a concentric inner channel 410. A cavity in which the increased-diameter portion 330 of the rod element 300 is seated is formed in the concentric inner channel 410 at a portion thereof. The axial end surfaces of the cavity in the vicinity of the bottom of the rod element holder 400 form respective stops for the axial end surfaces of the increased-diameter portion 330. Thus, in this embodiment, the rod element 300 cannot axially move at all, or only with a slight play, relative to the rod element holder 400.

The cylinder element 420 of the rod element holder 400 has a catheter connecting element 430 on a portion of its outer peripheral side. In the present embodiment, the catheter connecting element 430 extends at an acute angle relative to the cylinder element 420 of the rod element 400, as can be seen from the drawings.

In particular, the catheter connecting element 430 is formed as a hollow profile which basically constitutes a channel branch from the distal cavity of the cylinder element 420. The catheter connecting element 430 is formed as a cylinder, tapering in the direction away from the cylinder element 420. In its interior, the catheter connecting element 430 has a concentric channel in which the wire bodies are guided. The catheter connecting element 430 has a circular port at its distal end.

The catheter tube 500 is fixed to the circular port of the catheter connecting element 430. In particular, the proximal end 510 of the catheter tube 500 is seated at the port of the catheter connecting element 430.

At its distal end, the catheter tube has a ring 520 incorporated therein. The ring 520 forms the distal end of the catheter tube and the transition to the deflecting portion 600.

The catheter tube 500 and the deflecting portion 600 are constructed similarly to the catheter tube 5 and the deflecting portion 6 of the first embodiment.

In a similar manner as in FIG. 4, also the wire elements of the second embodiment are engaged in hang-in cavities of the control element. The description in connection with the wire elements of the first embodiment also applies to the second embodiment, and will not be repeated. The construction, the guide and the function of the wire elements are equal.

In the second embodiment, only the wire guiding ring 700 has a further function additionally to its construction described in the first embodiment. The wire guiding ring 700 as such is constructed in the same way as in the first embodiment. The wire guiding ring 700 of the second embodiment is displaceable longitudinally to the cylinder element 420 of the rod element holder 400. For this purpose, the cylinder element 420 of the rod element holder 400 comprises an axial longitudinal slit not shown in the drawings, along which the fixing screw, which engages in the threaded hole 72 (FIG. 4) and is adapted to fix the wire guiding ring 700 to the cylinder element 420 of the rod element holder 400, can be tightened at various positions.

When doing so, the wires can be tensioned by the ring element 700 being shifted in the axial direction into the cavity of the cylinder element 420 of the rod element holder 400 and then being locked by a locking element. In this way, the angle of the deflection point of the wires changes at the outlet of the ring element 700, i.e. on the right side of the ring element 700 in FIG. 9. In other words, when the wires are tensioned, the obtuse angle of the deflection point of the wires at the downstream outlet of the ring element 700 is reduced between the extension of the wires from the hang-in point to the ring element 700 and the extension of the wires from the ring element 700 to the catheter tube 500. In this way, small tension lengths of the wires can be realized.

The wire bodies are guided through the catheter tube 500 and through the ring 520 of the catheter tube and are anchored to the deflecting cap 620 of the deflecting portion 600. In particular, the wire bodies are anchored to the deflecting cap 620 such that they are evenly spaced from each other and are arranged in the same order as on the pivot portion 110.

The ring 520 comprises openings for the wire bodies in an analogous manner as in the design of the wire guiding ring 700.

The length of each wire body from the attachment point on the deflecting cap 620 to the attachment point on the pivot portion 110 is always the same.

Functioning/Operation

In a similar manner as in the first embodiment, also the control element 100 of the second embodiment can be operated as a joystick, wherein the foot surface 110A of the hollow ball portion 110 rolls on the front surface 310A of the head portion 310. In this way, it is possible to pivot the joystick 100 relatively to the rod element 300 in any direction whatsoever. The direction and the extent of the deflecting movement of the joystick 100 relative to the rod element 300 is then transferred by the wire bodies arranged on the deflecting cap 620 to the deflecting portion 600 configured as a bendable body.

When the joystick 100 is moved to the left relative to the rod element 300, the deflecting portion 600 executes a movement to the left, as is shown in FIG. 10. When the joystick 100 is moved to the right relative to the rod element 300, the deflecting portion 600 executes a movement to the right, as is shown in FIG. 11.

Prior to the introduction of the deflecting portion 600, the control element 100 is set straight, so that the deflecting portion 600 and the portion of the catheter tube 500 which is adjacent to the deflecting portion 600 are made to be straight. The distal end (on the deflecting cap 620) of the deflecting portion 600 is inserted into the funnel-shaped inlet opening of the inner channel 160 in the control element 100, is slid through the inner channel 160, is inserted into the inlet opening of the inner channel 350 in the rod element 300, which is adjacent to the outlet opening of the inner channel 160, and is pushed through the inner channel 350 until the deflecting portion 600 emerges at the outlet opening of the inner channel 350 which is opposite to the funnel-shaped inlet opening of the inner channel 350.

When the deflecting portion 600 has reached its intended operational position, i.e. the position in which it is slid through the secondary endoscope, the deflecting portion 600 can be brought into the desired position by turning the control element 100 in the desired direction and to the desired extent.

Alternatives of the Secondary Endoscope

The wire body 2 is engaged in the hang-in cavity 14 shown in FIG. 4 in the form of a barrel nipple 21. The invention is not restricted to a barrel nipple and the nipple 21 can be designed as a known pear nipple, any similar nipples may be used. The shape of the hang-in cavity 14 can be adapted to the selected nipple shape.

In the first embodiment, the size of the hollow ball portion 11 has been selected such that it amounts to 9/10 of a ball. The invention is not restricted thereto. Any hollow ball shape size of the hollow ball portion 11 can be selected as long as it can still carry out the pivot movement on the counter-ball portion 31. The hollow ball portion 11 can also have a hollow ball ring portion shape, which extends by a predetermined minimum dimension in parallel to the axial direction of the control element 1 at both sides of the equatorial line and basically forms an equatorial band/belt.

In the second embodiment, the foot surface 110A is outwardly bulged. Moreover, the front surface 310A of the head portion 310 is outwardly bulged. The invention is not restricted thereto. Using the principle of the invention, the secondary endoscope can also be constructed such that the foot surface 110A is plane and the front surface 310A is outwardly bulged. On the other hand, the secondary endoscope can also be constructed such that the foot surface 110A is outwardly bulged and the front surface 310A is plane. Another construction conceivable may be one in which the front surface 310A is bulged inwardly and the foot surface 110A is bulged outwardly, if the radius of curvature of the front surface 310A is larger than the radius of curvature of the foot surface 110A. In a similar way, the front surface 310A can be bulged outwardly and the foot surface 110A can be bulged inwardly, if the radius of curvature of the front surface 310A is smaller than the radius of curvature of the foot surface 110A. It is only sufficient that the foot surface 110A can roll on the front surface 310A in a safe and controlled manner.

In the first embodiment, the square end 34 serves to allow a screwing movement in order to carry out a relative movement of the rod element 3 to the rod element holder 4 on the threaded portions 33 and 41 so as to tension the wire bodies 2. The invention is not restricted to the square shape at the end 34 of the rod element 3. A triangular shape, octagonal shape, or another polygonal shape can be selected. In principle, any possible shape allowing the engagement of a torque/moment generating the rotational movement of the rod element on the end 34 can be selected.

In the first embodiment, the relative movement of the rod element 3 to the rod element holder 4 is carried out by the thread portions 33 and 41. The wire bodies 2 are tensioned by the movement of the rod element 3 relative to the rod element holder 4. Any other type of movement of the rod element 3 to the rod element holder 4 can be selected for this purpose. For instance, the rod element holder 4 can comprise a continuous inner cylinder hole and the rod element 3 can have a continuously cylindrical longitudinal cylinder 32, wherein a tensioning means is mounted on the end 34 of the rod element 3. A threaded bore can be provided in the rod element holder 4 perpendicularly to the axis of the rod element holder for holding a fixing screw adapted to lock the longitudinal cylinder 32 in any position relative to the rod element holder 4.

In the first embodiment, the rod element 3 is adapted to be concentrically screwed in or out relative to the rod element holder 4 by a screwing movement, wherein, during the screwing movement, the internal thread 41 of the rod element holder 4 is in threaded engagement with the external thread 33 of the rod element 3. In this design, the wires 2 are capable of being tensioned by the rod element 3 being moved and locked relative to the rod element holder 4.

In the second embodiment, the rod element 300 is positioned in the rod element holder 400, in which the increased-diameter portion 330 is arranged in a cavity of the rod element holder 400 provided therefor. The distal and proximal end faces of the increased-diameter portion 330 form a stop on the cavity of the rod element holder 400, respectively. In this construction, the wires are capable of being tensioned by the ring element 700 being shifted in the axial direction into the cavity of the cylinder element 420 of the rod element holder 400 and is then locked by a locking element.

The invention is not restricted thereto. In the first embodiment, the wire-tensioning possibility provided for the second embodiment can be used; and, in the second embodiment, the wire-tensioning possibility provided for the first embodiment can be used.

In the embodiments, the catheter connecting element 43; 430 extends at an acute angle, in consideration of the Figures, with respect to the rod element holder 4; 400. The invention is not restricted thereto. Any extension angle of the catheter connecting element to the rod element holder can be selected.

In the embodiments, the catheter tube 5; 500 is a transfer guiding body which has a cavity in which the movement transferring wire body is guided. In a pivoting movement of the control element, the movement transferring wire bodies 2 are exposed to pulling forces and pushing forces. When said pulling forces and pushing forces are exerted thereon, the movement transferring wire bodies 2 have to be capable of sliding on the transfer guiding body. The transfer guiding body can have a closed cross-section, as this is the case with respect to a catheter tube 5; 500. The invention is not restricted thereto. The transfer guiding body can be a rail element or box element on which the movement transferring wire body is guided. The cross-section of the transfer guiding body can be open on the side on which the movement transferring wire bodies 2 do not slide.

The control element 1; 100 can be lockable so as to lock a deflection position of the control element 1; 100. In the first embodiment, the locking can take place by a locking screw which e.g. penetrates the hollow ball portion 11 and engages with the surface of the counter-ball portion 31, thus acting as friction brake such that a specific deflection position of the control element 1, i.e. of the control lever, is lockable by the friction brake. Moreover, in all embodiments, locking can take place by the movement transferring wire body/bodies 2 being e.g. clamped on the wire guiding ring 7; 700 or on the cylinder element 42; 420 of the rod element holder 4; 400. Should all wires 2 e.g. be locked by a locking clamp attached to the wire guiding ring 7; 700 or to the cylinder element 42; 420, this leads to a safe locking of a deflection position of the control element 1; 100. Other technical possibilities for locking the wires 2 can be selected.

Assembly on the Mother Endoscope

FIG. 11 shows a schematic sectional view of the secondary endoscope of the second embodiment, wherein a mounting body for the assembly on the mother endoscope is disposed on the distal side of the grip body.

As is shown in FIG. 11, a connecting piece 1001 is disposed on the distal end of the inner channel acting as catheter channel. The connecting piece 1001 is a tube element. The tube element makes the inner channel longer. The proximal end of the connecting piece 1001 is non-rotatably connected to the distal end of the rod element holder 4 forming the grip body of the secondary endoscope. The distal end of the connecting piece 1001 is non-rotatably connected to a proximal end of a mounting body 1000 of the secondary endoscope. The mounting body 1000 is also hollow and makes the inner channel longer.

The mounting body 1000 of the secondary endoscope is used for the assembly of the secondary endoscope on the mother endoscope and forms an assembly unit with a mounting body 2440 of the mother endoscope as described below.

In the present embodiment, the mounting body 1000 is formed as a Luer lock male element. The assembly unit is formed by a Luer lock connection having an axially extending inner channel.

The Luer lock male element 1000 is an element of said Luer lock connection. Luer lock connections are standardized connections which are frequently used in the medical sector.

In particular, the hollow Luer lock male element 1000 has a hollow grip element 1002 on its proximal side and a hollow Luer lock cone 1003, the proximal portion of which is surrounded by a Luer lock sleeve 1004 on its distal side. The proximal end of the Luer lock sleeve 1004 abuts on the distal end of the grip element 1002 and is connected thereto. As the exact structure of a Luer lock connection is known to those skilled in the art, this will not be specified any further here.

On its outer circumferential surface, the grip element 1002 can be provided with a fluting. On its outer circumferential surface, the grip element 1002 can be provided, alternatively or additionally, with a marking for providing information on the mounted or demounted state. This means that, when the Luer lock connection is closed, this is indicated to the user by a marking; and, when the Luer lock connection is opened, this will also be indicated to the user by a marking. Such an indicative marking may e.g. be an extendable and retractable projection, which e.g. indicates a closed connection in its retracted position and an open connection in its extended position. In this way, the user can also recognize the information that the connection is not safely connected by means of keys. The extendable and retractable projection is adapted to have a red colored circumferential edge, which is recessed in its retracted state and visible to the user in its extended state and provides information on the open connection.

Alternatively, the mounting body 1000 can be a screw top element, a bayonet locking element or a snap connection element and can, accordingly, form a detachable screw connection, bayonet locking connection or snap connection with the mounting body 2440 of the mother endoscope. In any case, said detachable mounting connection comprises an inner channel and a locking. The locking is preferably not detachable by the user and can e.g. be opened by the manufacturer of the device or in a maintenance and repair center authorized to do so.

Combination of Mother Endoscope and Secondary Endoscope

Figure 12:
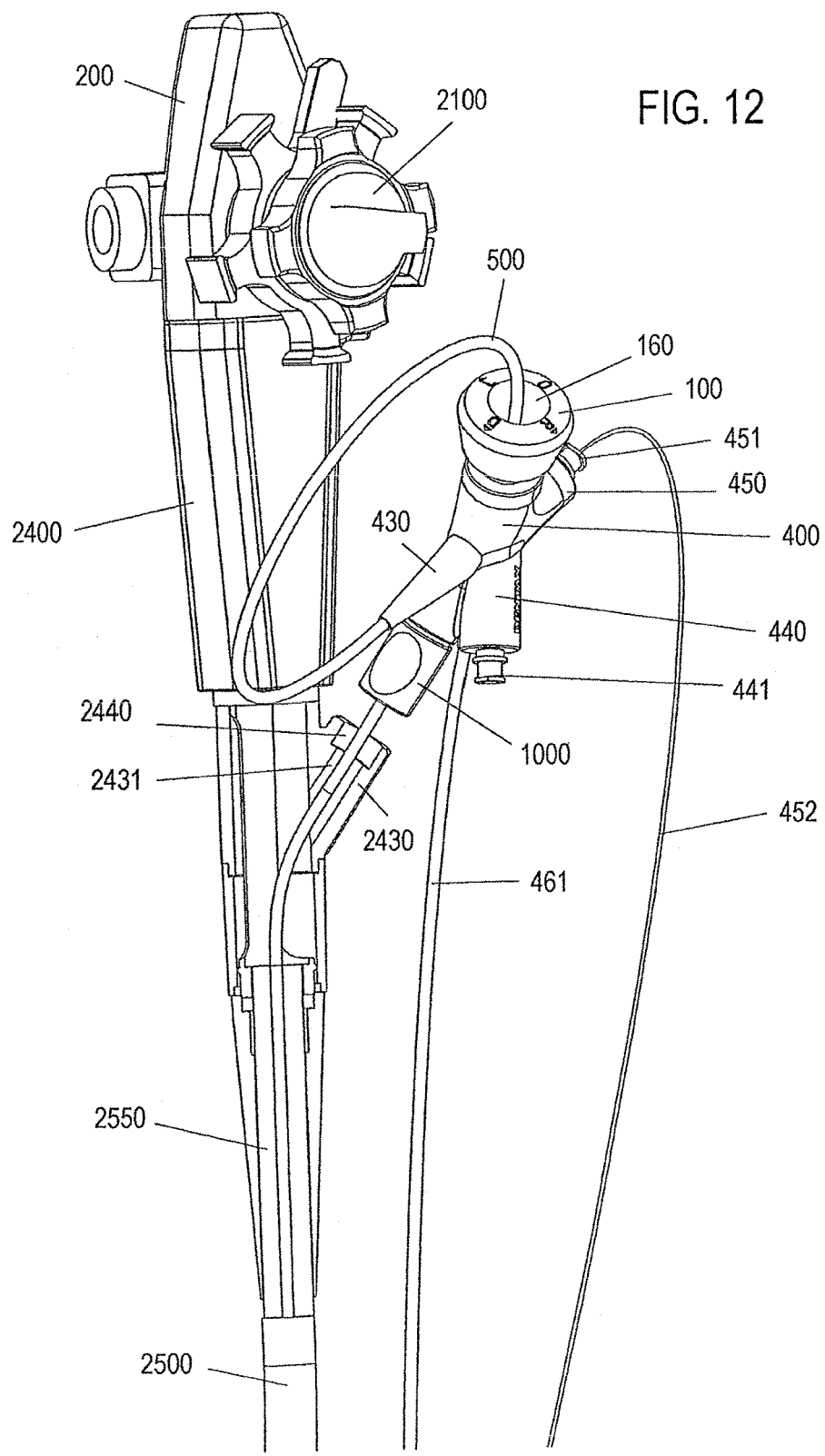
FIG. 12 shows a schematic sectional view of a combination of a mother endoscope and the inventive secondary endoscope.

FIG. 12 shows a schematic partial-section view of a combination of a mother endoscope and the secondary endoscope according to the invention.

A mother endoscope 200 has a control element 2100 on a mother endoscope grip 2400. On the distal side of the mother endoscope grip 2400, an access connecting piece 2430 for a secondary endoscope extends at a predetermined angle, which can amount to 45°. The predetermined angle is not limited to 45°.

A mother endoscope 200 has a centrically provided working channel 2550, which continues in the tube element 2500 of the mother endoscope. A working channel branch 2431 branches off the working channel 2550 into the access connecting piece 2430. In the access connecting piece 2430, the working channel branch 2431 also extends centrically. Thus, the outlet of the working channel branch 2431 leads into the working channel 2550 of the mother endoscope. The inlet of the working channel branch 2431 has an opening on the proximal side of the access connecting piece 2430. To this opening, a Luer lock female element 2440 is non-rotatably mounted as mounting body for the connection with the secondary endoscope. The Luer lock female element 2440 is also designated as sleeve.

An inventive secondary endoscope is mounted on the Luer lock female element 2440. When doing so, the mounting body 1000 of the secondary endoscope is connected to the mounting body 2440 of the mother endoscope and is locked.

The secondary endoscope according to FIG. 12 is an inventive secondary endoscope according to the above-described embodiments, which can be provided with further functional units, as will be described below. The secondary endoscope has the grip body 400 in which the catheter channel 410 is formed. As is shown in FIG. 12, the grip body 400 has the control element 160 on its proximal side. Also on the proximal side of the grip body 400, there is arranged an additional channel connecting element 450, which extends at an angle away from the grip body 400, e.g. in the proximal direction. In the additional channel connecting element 450, an additional channel extends into the grip body 400 and leads into the inner channel/catheter channel. Further medical instruments can be inserted into the additional channel. One example of such an instrument is a laser cable 452.

On the proximal side of the additional channel connecting element 450, there is arranged an additional channel inlet opening 451 into which the laser cable 452 is inserted. On the distal side, the grip body 400 has the mounting body 1000, as has already been described. Also on the distal side of the grip body 400, there is arranged a flushing channel connecting element 440, which extends at an angle from the grip body 400, e.g. in the distal direction. There is a flushing channel inlet opening 441 on the distal side of the flushing channel connecting element 440. The grip body 400 further has a power cable 461 on its distal side.

As has already been described, the grip body 400 further has, on its distal side, the catheter connecting element 430, from which the catheter tube 500 distally extends. The catheter tube 500 is inserted into the inlet opening of the catheter channel 160 of the control element 100 and extends through the catheter channel 410, which is not shown in FIG. 12, through the inner channel of the mounting body 1000 of the secondary endoscope, through the inner channel of the mounting body 2440 of the mother endoscope, through the working channel branch 2431 and through the working channel 2550 of the mother endoscope until reaching its deflecting portion 600. The deflecting portion 600 is pivoted by a pivoting movement of the control element 100.

The control element 100 can be provided with markings indicating to the user the pivoting directions for the deflecting portion 600. For example, the deflecting portion 600 can be pivoted to the right by the control element 100 being pivoted to the right, i.e. in the direction which is indicated by the marking "R". The deflecting portion 600 can be pivoted to the left by the control element 100 being pivoted to the left, i.e. in the direction indicated by the marking "L". The deflecting portion 600 is accordingly pivoted downwards or upwards in dependence on the control element 100 being pivoted in the other directions indicated by markings "D" or "U". As the control element 100 can be pivoted in all directions, the deflecting portion 600, as well, can be pivoted in all directions.

ADVANTAGES OF THE INVENTION

By the specific arrangement of the catheter tube 500 in the catheter channel 160, 410 of the secondary endoscope grip body 400, the catheter basically forms a loop in itself. Moreover, the catheter channel 160, 410 in the secondary endoscope can be formed to be exceptionally short, which leads to an extremely small structure of the secondary endoscope as such. This makes the operation for the user simpler and clearer, as the catheter tube 500 does not constitute an obstacle to the user. The operability of the control element as a joystick makes handling easier. The secondary endoscope is operable by a user using one hand. Moreover, the secondary endoscope can be manufactured cost-effectively due to its simple design.

LIST OF REFERENCE SIGNS

1 control element; joystick
2, 2*a*, 2*b* wire body
3 base element; rod element
4 rod element holder; grip body of the secondary endoscope
5 catheter tube
6 deflecting portion
7 wire guiding ring
11 hollow ball portion
11A foot surface of the hollow ball portion 11
12 head of the control element 1
13 shaft portion
14 hang-in cavity
15 wire body hang-in
16 inner channel in the control element; catheter channel
21 barrel nipple
31 head portion; counter-ball portion
31A front surface of the head portion 31
32 longitudinal cylinder
33 threaded portion of the rod element 3
34 square end; distal end of the rod element 3
35 inner channel in the rod element; catheter channel
41 threaded portion of the rod element holder 4
42 cylinder element
43 catheter connecting element
51 catheter tube connection
52 ring
61 deflecting connection
62 deflecting cap
71 wire guiding bore
72 threaded hole for a fixing screw
100 control element; joystick
110 hollow ball portion
110A foot surface of the hollow ball portion 110
120 head of the control element 100
130 shaft portion
160 inner channel in the control element; catheter channel
200 mother endoscope
300 base element; rod element
310 head portion; counter-ball portion
310A front surface of the head portion 31
320 longitudinal cylinder
330 increased-diameter portion
350 inner channel in the rod element; catheter channel
400 rod element holder; grip body of the secondary endoscope
410 inner channel in the rod element
420 cylinder element
430 catheter connecting element
440 flushing channel connecting element
441 flushing channel inlet opening
450 additional channel connecting element
451 additional channel inlet opening
452 laser cable
461 power cable
500 catheter tube
510 catheter tube connection
520 ring
600 deflecting portion
610 deflecting connection
620 deflecting cap
700 wire guiding ring
1000 Luer lock male member; mounting body
1001 connecting piece
1002 grip element
1003 Luer lock cone
1004 Luer lock sleeve
2100 control element
2400 mother endoscope grip
2430 access connecting piece for a secondary endoscope
2431 working channel branch in the access connecting piece
2440 Luer lock female member; mounting body
2500 tube element of the mother endoscope
2550 working channel in the mother endoscope

The invention claimed is:

1. A secondary endoscope mountable onto a mother endoscope, comprising
a grip body having a proximal side and a distal end and comprising an outer body including an inner channel, the grip body further having an inner body arranged in the inner channel of the outer body, said inner body being movable relative to the outer body;
a catheter mounted in the grip body and having a distal end comprising a bendable portion;
a control element at the proximal side of the grip body for controlling the bendable portion, said control element being arranged on the proximal side of the inner body; and
a mounting connection on the distal end of the grip body for fixing the secondary endoscope to a mother endoscope, said mounting connection being attached to the outer body of the grip body
wherein the control element is pivotable relative to the inner body, and
wherein to the control element a control wire is attached, wherein the control wire is guided in the outer body of the grip body, and the control wire is attached to the bendable portion.

2. The secondary endoscope according to claim 1, wherein
the grip body comprises a catheter channel for guiding the catheter.

3. The secondary endoscope according to claim 2, wherein the control element has a proximal end comprising a proximal inlet opening for the catheter channel.

4. The secondary endoscope according to claim 1, wherein
the catheter has a proximal end mounted on the distal side of the grip body.

5. The secondary endoscope according to claim 1, wherein
the proximal end of the catheter is mounted on the outer side of the grip body.

6. The secondary endoscope according to claim 1, wherein
the distal end of the grip body comprises a mounting body for being assembled with the mother endoscope, said mounting body comprising a section of the catheter channel for guiding the catheter.

7. The secondary endoscope according to claim 6, wherein
the mounting body is provided with a marking providing information on the mounted or demounted state.

8. The secondary endoscope according to claim 6, wherein
the mounting body is a Luer lock connecting element, a screw top element, a bayonet locking element, or a snap connection element.

9. The secondary endoscope according to claim 1, wherein
the control element is pivotable for pivoting the bendable portion of the catheter and is provided, on its proximal side, with markings providing information on the pivoting direction of the bendable portion.

10. The secondary endoscope according to claim 1, wherein
the catheter is mounted on the outer body of the grip body.

11. A combination of a mother endo scope and a secondary endoscope, comprising
a mother endoscope including an access connecting piece for a secondary endoscope; and
a secondary endoscope mountable onto the mother endoscope, comprising
a grip body having a proximal side and a distal end and comprising an outer body including an inner channel, the grip body further having an inner body arranged in the inner channel of the outer body, said inner body being movable relatively to the outer body;
a catheter mounted on in the grip body and having a distal end comprising a bendable portion;
a control element at the proximal side of the grip body for controlling the bendable portion arranged on the distal end of the catheter, said control element being arranged on the proximal side of the inner body; and
a mounting connection on the distal end of the grip body for fixing the secondary endoscope to the mother endoscope, said mounting connection being attached to the outer body of the grip body;
wherein the control element is pivotable relative to the inner body, and
wherein to the control element a control wire is attached, wherein the control wire is guided in the outer body of the grip body, and the control wire is attached to the bendable portion.

12. A combination of a mother endoscope and a secondary endoscope, comprising
a mother endoscope having a grip and an access connecting piece distal of the grip for a secondary endoscope on the distal side of a mother endoscope grip; and
a secondary endoscope detachably mounted to the access connecting piece and comprising
a grip body having a proximal side and a distal end and comprising an outer body including an inner channel, the grip body further having an inner body arranged in the inner channel of the outer body, said inner body being movable relatively to the outer body;
a catheter mounted in the grip body and having a distal end comprising a bendable portion;
a control element at the proximal side of the grip body for controlling the bendable portion arranged on the distal end of the catheter, said control element being arranged on the proximal side of the inner body; and
a mounting connection on the distal end of the grip body for fixing the secondary endoscope to the mother endoscope, said mounting connection being attached to the outer body of the grip body;
wherein the catheter of the secondary endoscope is guided through a catheter channel of the grip body;
wherein the distal end of the grip body is detachably mounted on the access connecting piece of the mother endoscope;
wherein, in its mounted position, the secondary endoscope on the mother endoscope grip is detachably mounted on the proximal side of the access connecting piece of the mother endoscope;
wherein a catheter inlet opening is positioned on the secondary endoscope proximally from the mounting place of the secondary endoscope;
wherein the control element is pivotable relative to the inner body, and
wherein to the control element a control wire is attached, wherein the control wire is guided in the outer body of the grip body, and the control wire is attached to the bendable portion.

13. The combination according to claim 12, wherein
the grip body further comprises an additional channel inlet opening on the proximal side and a fluid inlet opening on the distal side.

* * * * *